US010316286B1

(12) United States Patent
Yi et al.

(10) Patent No.: US 10,316,286 B1
(45) Date of Patent: Jun. 11, 2019

(54) METHODS FOR GENERATION OF CYTOCAPSULAE AND CYTOCAPSULAR TUBES

(71) Applicant: Cellmig Biolabs Inc., Cambridge, MA (US)

(72) Inventors: Tingfang Yi, Chestnut Hill, MA (US); Gerhard Wagner, Chestnut Hill, MA (US)

(73) Assignee: Cellmig Biolabs Inc., Cambridge, MA (US)

( * ) Notice: Subject to any disclaimer, the term of this patent is extended or adjusted under 35 U.S.C. 154(b) by 0 days.

(21) Appl. No.: 15/939,366

(22) Filed: Mar. 29, 2018

Related U.S. Application Data

(63) Continuation of application No. PCT/US2018/013470, filed on Jan. 12, 2018.

(51) Int. Cl.
*C12N 5/00* (2006.01)
*C12N 5/071* (2010.01)
*C12N 5/095* (2010.01)
*C12M 1/24* (2006.01)
*C12M 1/12* (2006.01)
*C12M 1/00* (2006.01)

(52) U.S. Cl.
CPC ......... *C12N 5/0068* (2013.01); *C12N 5/0631* (2013.01); *C12N 5/0695* (2013.01); *C12N 2533/90* (2013.01)

(58) Field of Classification Search
CPC .................................................. C12N 5/0631
See application file for complete search history.

(56) References Cited

PUBLICATIONS

Bergstraesser et al "Culture of normal and malignant primary human mammary epithelial cells in a physiological manner simulates in vivo grown patterns and allows discrimination of cell type" Cancer Research, 1993, vol. 53, pp. 2644-2654. (Year: 1993).*
Gomm et al, "Separated human breast epithelial and myoepithelial cells have different growth factor requirements in vitro but can reconstitute normal breast lobuloalveolar structure" Journal of Cellular Physiology, 1997, vol. 171, pp. 11-19. (Year: 1997).*
Mullen, Peter. "Section Title." Cancer Cell Culture: Methods and Protocols. Ed. Simon P Langdon. Totowa, NJ: Humana Press, 2003. 287-291. Print. (Year: 2003).*
Yi et al, "Cytocapsular tubes conduct cell translocation" PNAS 2018, 115 (6): E1137-E1146 (Year: 2018).*
Acloque, Herve, et al.,"Epithelial-mesenchymal transitions: the importance of changing cell state in development and disease." The Journal of Clinical Investigation, 2009; 119(6): 1438-1449.
Baker, Brendon M., et al.,"Deconstructing the third dimension—how 3D culture microenvironments alter cellular cues," Journal of Cell Science 125, 3015-3024, 2012, The Company of Biologists Ltd.
Bonnanas, Caroline, et al.,"Remodelling the extracellular matrix in development and disease," Nature Reviews: Molecular Cell Biology, Dec. 2014, 786-801 , vol. 15, Macmillan Publishers Limited.
Bryant, David M., et al.,"From cells to organs: building polarized tissue," Nature Reviews: Molecular Cell Biology, Nov. 2008, pp. 887-901, vol. 9, Macmillan Publishers Limited.
Chebli, Youssef, et al.,"Cellular growth in plants requires regulation of cell wall biochemistry," Current Opinion in Cell Biology, 2017, 44:28-35, Elsevier Ltd.
Chen, Wen-Tien, et al.,"Proteolytic Activity of Specialized Surface Protrusions Formed at Rosette Contact Sites of Transformed Cells," The Journal of Experimental Zoology, Dec. 18, 1989, vol. 251: pp. 167-185, Alan R. Liss, Inc.
Dong, Haohao, et al.,"Structural insight into lipopolysaccharide transport from the Gram-negative bacterial inner membrane to the outer membrane," BBA—Molecular and Cell Biology of Lipids, Jun. 28, 2017, pp. 1461-1467, vol. 1862, Elsevier BV.
Egeblad, Mikala, et al.,"New Functions for the Matrix Metalloproteinases in Cancer Progression," Nature Reviews, Mar. 2002, vol. 2, pp. 161-174, Department of Anatomy, University of California, San Francisco.
Fackler, Oliver T., et al.,"Cell Motility through Plasma Membrane Blebbing," The Journal of Cell Biology, Jun. 9, 2008, pp. 879-884, vol. 181 No. 6, The Rockefeller University Press.
Franz, Clemens M., et al.,"Cell Migration in Development and Disease," Meeting Review, Feb. 2002, pp. 153-158, vol. 2, Cell Press.
Friedl, Peter, et al.,"Cancer Invasion and the Microenvironment: Plasticity and Reciprocity," Cell, Nov. 23, 2011, pp. 992-1009, vol. 147, Elsevier Inc.
Friedl, Peter, et al.,"New Dimensions in Cell Migration," Nature Reviews | Molecular Cell Biology, Nov. 2012, pp. 743-747, vol. 13, Macmillan Publishers Limited.
Friedl, Peter, et al.,"Tumour-cell Invasion and Migration: Diversity and Escape Mechanisms," Nature, May 2003, pp. 362-374, vol. 3, Nature Publishing Group.
Gingras, Anne-Claude, et al.,"Regulation of 4E-BP1 Phosphorylation: A Novel two-step Mechanism," Genes & Development, Feb. 22, 1999, pp. 1422-1437, vol. 13, Cold Spring Harbor Laboratory Press.
Giri, Anjil, et al.,"The Arp2/3 Complex Mediates Multigeneration Dendritic Protrusions for Efficient 3-dimensional Cancer Cell Migration," The FASEB Journal, Oct. 2013, pp. 4089-4099, vol. 10, FASEB.
Gross, John D., et al.,"Ribosome Loading onto the mRNA Cap Is Driven by Conformational Coupling between eIF4G and eIF4E," Cell, pp. 739-750, vol. 115, Cell Press.
Gurtner, Geoffrey C., et al.,"Wound Repair and Regeneration," Nature, May 15, 2008, pp. 314-321, vol. 453, Nature Publishing Group.
Heldin, Carl-Henrik, et al.,"Signal Transduction via Platelet-derived Growth Factor Receptors," Biocjo,oca et Biophysica Acta, Feb. 9, 1998, pp. F79-F113, vol. 1378, Elsevier Science BV.
Jayatilaka, Hasini, et al.,"Synergistic IL-6 and IL-8 Paracrine Signalling Pathway infers a Strategy to Inhibit Tumour Cell Migration," Nature Communications, May 26, 2017, pp. 1-12, vol. 8, 15584.

(Continued)

*Primary Examiner* — Allison M Fox
(74) *Attorney, Agent, or Firm* — Banner & Witcoff, Ltd.

(57) ABSTRACT

This invention provides for methods and compositions for generation of cytocapsulae and cytocapsular tubes in a 3D matrix.

20 Claims, 11 Drawing Sheets

(56) References Cited

PUBLICATIONS

Johnstone, Rose M., et al., "Vesicle Formation during Reticulocyte Maturation," The Journal of Biological Chemistry, Jul. 5, 1987, pp. 9412-9420, vol. 262, No. 19, The American Society of Biological Chemists, Inc.

Keller, Sascha, et al., "Exosomes: From Biogenesis and Secretion to Biological Function," Science Direct, Sep. 13, 2006, pp. 102-108, vol. 107, Elsevier BV.

Le Douarin, Nicole M., "Cell Migrations in Embryos," Cell, Sep. 1984, pp. 353-360, vol. 38, MIT.

Marintchev, Assen, et al., "Topology and Regulation of the Human eIF4A/4G/4H Helicase Complex in Translation Initiation," Cell, Feb. 6, 2009 pp. 447-460, vol. 136, Elsevier Inc.

Mattila, Pieta K., "Filopodia: Molecular Architecture and Cellular Functions," Nature, Jun. 2008, pp. 446-454, vol. 9, Nature Publishing Group.

Moerke, Nathan J., et al., "Small-Molecule Inhibition of the Interaction between the Translation Initiation Factors eIF4E and eIF4G," Cell, Jan. 26, 2007, pp. 257-267, vol. 128, Elsevier Inc.

Murphy, Danielle A., et al., "The 'ins' and 'outs' of Podosomes and Invadopodia: Characteristics, Formation and Function," Nature Reviews | Molecular Cell Biology, Jul. 2011, pp. 413-426, vol. 12, Macmillan Publishers Limited.

Noble, Mark, et al., "Platelet-Derived Growth Factor Promotes Division and Motility and Inhibits Premature Differentiation of the Oligodendrocyte/type-2 Astrocyte Progenitor Cell," Nature, Jun. 9, 1988, pp. 560-562, vol. 333, Nature Publishing Group.

Petrie, Ryan J., et al., "Random Versus Directionally Persistent Cell Migration," Nature, Aug. 2009, pp. 538-549, vol. 10, Macmillan Publishers Limited.

Reig, German, et al., "Cell Migration: From Tissue Culture to Embryos," Development, 2014, pp. 1999-2013, vol. 141, The Company of Biologists Ltd.

Richardson, Brian E., et al., "Mechanisms Guiding Primordial Germ Cell Migration: Strategies from Different Organisms," Nature Reviews | Molecular Cell Biology, Jan. 2010, pp. 37-49, vol. 11, Macmillan Publishers Limited.

Ridley, Anne J., "Life at the Leading Edge," Cell, Jun. 24, 2011, pp. 1012-1022, vol. 145, Elsevier Inc.

Satir, Peter, "CILIA: Before and After," Cilia, Feb. 8, 2017, pp. 1-11, vol. 6 No. 1, BioMed Central.

Silvera, Deborah, et al., "Translational Control in Cancer," Nature Reviews, Apr. 2010, pp. 254-266, vol. 10, Macmillan Publishers Limited.

Tarone, Guido, et al., "Rous Sarcoma Virus-Transformed Fibroblasts Adhere Primarily at Discrete Protrusions of the Ventral Membrane Called Podosomes," Experimental Cell Research, 1985, pp. 141-157, vol. 159, Academic Press, Inc.

Thery, Clotilde, et al., "Exosomes: Composition, Biogenesis and Function," Nature Reviews | Immunology, Aug. 2002, pp. 569-579, vol. 2.

Thiery, Jean Paul, et al., "Epithelial-Mesenchymal Transitions in Development and Disease," Cell, Nov. 25, 2009, pp. 871-890, vol. 139, Elsevier Inc.

Wehrle-Haller, Bernhard, "Structure and Function of Focal Adhesions" Current Opinion in Cell Biology, 2012, pp. 116-124, vol. 24, Elsevier Ltd.

Weninger, Wolfgang, et al., "Leukocyte Migration in the Interstitial Space of Non-Lymphoid Organs," Nature Reviews, Apr. 2014, pp. 232-246, vol. 14, Macmillan Publishers Limited.

Wolf, Katarina, et al. "Multi-step Pericellular Proteolysis Controls the Transition from Individual to Collective Cancer Cell Invasion," Nature Cell Biology, Aug. 2007, pp. 893-904, vol. 9, No. 8, Nature Publishing Group.

Woodland, David L., et al., "Migration, Maintenance and Recall of Memory T Cells in Peripheral Tissues," Nature Reviews | Immunology, Mar. 2009, pp. 153-161, vol. 9, Macmillan Publishers Limited.

Wu, Pei-Hsun, et al., "Three-Dimensional Cell Migration Does Not Follow a Random Walk," PNAS, Mar. 18, 2014, pp. 3949-3954, vol. 111, No. 11.

Yi, Tingfang, et al., "Quantitative Phosphoproteomic Analysis Reveals System-wide Signaling Pathways Downstream of SDF-1/CXCR4 in Breast Cancer Stem Cells," PNAS, Apr. 29, 2014, E2182-E2190.

Yoshida, Kanako, et al., "Role of Bacterial Capsule in Local and Systemic Inflammatory Responses of Mice during Pulmonary Infection with Klebsiella Pneumoniae," J. Med. Microbiol., Mar. 27, 2000, pp. 1003-1010, vol. 49, The Pathological Society of Great Britain and Ireland.

Zani, Brett G., et al., "Tubular Bridges for Bronchial Epithelial Cell Migration and Communication," PLoS ONE, Jan. 2010, pp. 1-12, vol. 5, No. 1, e8930.

\* cited by examiner

METHODS FOR GENERATION OF CYTOCAPSULAE AND CYTOCAPSULAR TUBES

RELATED APPLICATION DATA

This application is a continuation application which claims priority to PCT application PCT/US2018/013470 designating the United States and filed Jan. 12, 2018, the content of which is hereby incorporated by reference in its entirety.

FIELD

The invention is related to the area of generation of cytocapsulae and cytocapsular tubes, and methods and compositions thereof.

BACKGROUND

Cell boundary separates the cell from the outside environment, allowing and protecting intracellular activities and contents from undesired influence of environmental factors. Cellular boundary is essential for cell sensing, migration, invasion, relocation, proliferation, growth, differentiation, communication with and responding to environments, nutrient and oxygen intake, metabolite waste exclusion, and protection against environmental stress.

Cell locomotion in multicellular organism is critical for embryonic development (Le Douarin N M (1984) Cell migrations in embryos. *Cell* 38(2):353-360; Reig G, Pulgar E, & Concha M L (2014) Cell migration: from tissue culture to embryos. *Development* 141(10):1999-2013; Richardson B E & Lehmann R (2010) Mechanisms guiding primordial germ cell migration: strategies from different organisms. *Nat Rev Mol Cell Biol* 11(1):37-49), organ homeostasis (Acloque H, Adams M S, Fishwick K, Bronner-Fraser M, & Nieto M A (2009) Epithelial-mesenchymal transitions: the importance of changing cell state in development and disease. *The Journal of clinical investigation* 119(6):1438-1449), tissue regeneration (Bryant D M & Mostov K E (2008) From cells to organs: building polarized tissue. *Nat Rev Mol Cell Biol* 9(11):887-901), immunological responses (Woodland D L & Kohlmeier J E (2009) Migration, maintenance and recall of memory T cells in peripheral tissues. *Nat Rev Immunol* 9(3):153-161; Weninger W, Biro M, & Jain R (2014) Leukocyte migration in the interstitial space of non-lymphoid organs. *Nat Rev Immunol* 14(4):232-246), wound repair (Gurtner G C, Werner S, Barrandon Y, & Longaker M T (2008) Wound repair and regeneration. *Nature* 453(7193):314-321), and tumor dissemination (Friedl P & Alexander S (2011) Cancer invasion and the microenvironment: plasticity and reciprocity. *Cell* 147(5):992-1009; Friedl P & Wolf K (2003) Tumour-cell invasion and migration: diversity and escape mechanisms. *Nat Rev Cancer* 3(5):362-374; Barbolina M V, et al. (2009) Microenvironmental regulation of ovarian cancer metastasis. *Cancer Treat Res* 149:319-334). Cell migration in three dimensional (3D) microenvironments experience heterogeneous cells and extracellular matrices (ECM), which provide supporting scaffolds and guiding clues for locomotion directions and meanwhile substantially form environmental obstacles impeding cell motility (Thiery J P, Acloque H, Huang R Y, & Nieto M A (2009) Epithelial-mesenchymal transitions in development and disease. Cell 139(5):871-890; Franz C M, Jones G E, & Ridley A J (2002) Cell migration in development and disease. *Dev Cell* 2(2):153-158). To facilitate motility, cells adaptively generate temporospatial surface-connected organelles and compartments, including lamellipodia (Murphy D A & Courtneidge S A (2011) The 'ins' and 'outs' of podosomes and invadopodia: characteristics, formation and function. *Nat Rev Mol Cell Biol* 12(7):413-426), filopodia (Mattila P K & Lappalainen P (2008) Filopodia: molecular architecture and cellular functions. *Nat Rev Mol Cell Biol* 9(6):446-454), podosomes (Tarone G, Cirillo D, Giancotti F G, Comoglio P M, & Marchisio P C (1985) Rous sarcoma virus-transformed fibroblasts adhere primarily at discrete protrusions of the ventral membrane called podosomes. *Exp Cell Res* 159(1):141-157), invadopodia (Chen W T (1989) Proteolytic activity of specialized surface protrusions formed at rosette contact sites of transformed cells. *J Exp Zool* 251(2):167-185), blebs (Fackler O T & Grosse R (2008) Cell motility through plasma membrane blebbing. *J Cell Biol* 181(6):879-884; Ridley A J (2011) Life at the leading edge. *Cell* 145(7):1012-1022), focal adhesion (Wehrle-Haller B (2012) Structure and function of focal adhesions. *Current opinion in cell biology* 24(1):116-124), dendritic pseudopodial protrusion, and type II epithelial bridge (Zani B G, Indolfi L, & Edelman E R (2010) Tubular bridges for bronchial epithelial cell migration and communication. *PLoS One* 5(1):e8930). The mechanics of cell relocation in multicellular organism are therefore unclear.

The cellular morphology, employed organelles, and mechanical and signaling control in 3D cell migration are often different from their 2D counterparts (Baker B M & Chen C S (2012) Deconstructing the third dimension: how 3D culture microenvironments alter cellular cues. *J Cell Sci* 125(Pt 13):3015-3024; Wu P H, Giri A, Sun S X, & Wirtz D (2014) Three-dimensional cell migration does not follow a random walk. *Proceedings of the National Academy of Sciences of the United States of America* 111(11):3949-3954; Friedl P, Sahai E, Weiss S, & Yamada K M (2012) New dimensions in cell migration. *Nat Rev Mol Cell Biol* 13(11):743-747). Cells in locomotion in collagen-rich 3D matrix do not present lamellipodia or filopodia, but display highly dendritic pseudopodial protrusions, which are absent on rigid plate surfaces (Jayatilaka H, et al. (2017) Synergistic IL-6 and IL-8 paracrine signalling pathway infers a strategy to inhibit tumour cell migration. *Nature communications* 8:15584; Giri A, et al. (2013) The Arp2/3 complex mediates multigeneration dendritic protrusions for efficient 3-dimensional cancer cell migration. *FASEB journal: official publication of the Federation of American Societies for Experimental Biology* 27(10):4089-4099).

There is a continuing need in the art for methods and compositions useful for understanding cell locomotion in 3D extracellular matrix and 3D microenvironments.

SUMMARY

The present disclosure addresses this need and is based on the discovery that cells in controlled 3D microenvironments, such as a 3D extracellular matrix, can generate at least two types of novel membranous organelles, namely, cytocapsulae and cytocapsular tubes. The cytocapsular tubes provide tubular pathways for directed cell transportation. Multiple cytocapsular tubes interconnect and form networks of tubular webs for directed cell transportation in diverse directions. Enhanced cap-dependent translation initiation as well as increased expression of proteins including ITGB-2 has been found to be associated with cytocapsulae and cytocapsular tube formation and cytocapsular tube elongation. The methods and compositions for the generation of cytocapsula and cytocapsular tube in a controlled 3D extracellular matrix provides powerful tools for understanding the mechanisms underlying cell migration in 3D microenvironments, which is a prerequisite for the development of effective therapeutics against a wide range of diseases relating to cell migration, cell sensing, cell stress protection, cell proliferation, cell differentiation, tumor growth, tumor development, tumor metastasis, tumor relapse, and drug resistance.

According to one aspect of the present disclosure, a composition comprising a 3D extracellular matrix and cytocapsulae and cytocapsular tubes is provided. The cytocapsulae and cytocapsular tubes are generated by cells implanted in or on top of the 3D matrix.

According to another aspect of the present disclosure, a method of generating cytocapsulae and cytocapsular tubes is provided. The method includes implanting cells in or on top of a 3D matrix, and incubating the cell implanted 3D matrix under conditions such that the cells engender the cytocapsulae and cytocapsular tubes.

According to still another aspect of the present disclosure, a method of producing cytocapsulae and cytocapsular tubes in vitro is provided. The method includes the steps of: implanting cells in a single cell suspension onto the top layer of a 3D matrix; and culturing the cell implanted 3D matrix under conditions such that the cells engender cytocapsulae and cytocapsular tubes in the 3D matrix.

According to yet another aspect of the present disclosure, a method of preparing a 3D matrix suitable for the generation of cytocapsulae and cytocapsular tubes is provided. The method includes freezing the 3D matrix, and thawing the 3D matrix at a suitable temperature.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 1A shows an image of generation of cytocapsulae and elongated cytocapsular tubes. Human mammary epithelial cells (HMECs) implanted onto thick and 3D Matrigel gel under the indicated conditions generate membranous, extra-cytoplasmic cytocapsulae and elongated cytocapsular tubes. Fluoresence images of cytocapsular tubes of single HMECs, which are transiently overexpress EGFP-PMCA2 and mCherry-β-actin, with cytocapsular tubes are shown. HMECs (red arrows), cytocapsulae (CC, white arrow), cytocapsular membranes (CCM, orange arrows) are shown. FIG. 1B shows a quantitation analysis of cytocapsular tube lengths. FIG. 1C shows inverted phase contrast bright field microscope images of ecellularization of cytocapsulae. The blue arrow indicated single HMEC generates a large cytocapsula (CC, red arrow) enveloping the cell. After 1 h, the HMEC departs the cytocapsula leaving the ecellulated cytocapsula (eCC, white arrow) without cell inside. The cytocapsular membrane (CCM, orange arrow) is shown. FIG. 1D shows a schematic diagram of cytocapsula ecellularization. FIG. 1E shows a quantitative assay of cytocapsular sizes in diameter. FIG. 1F shows a DIC image (left panel) and fluoresence image (right panel) of a large membranous cytocapsula (CC, red arrows). Scale bar=10 μm.

(FIG. 3A) Multiple BCSC cytocapsular tube crosses. Multiple BCSC cytocapsular tubes interconnect via cytocapsular tube node (CTN) and form cross morphologies. Cells migrate in the cytocapsular tube networks. (FIG. 3B) BCSC cytocapsular tube (CT, red arrows) networks in radical morphologies. Up to five cytocapsular tubes connect via cytocapsular tube node (CTN). Multiple cells migrate in the cytocapsular tube networks in diverse morphologies. Scale bar=10 μm.

(FIG. 5A) Bright field image of a merged cytocapsular tube combined by the two cytocapsular tubes produced by two cells. Cell 2 is located in the merged cytocapsular tube. Merged cytocapsular tube (MTP, red arrow), merged cytocapsular tube membrane (MTM, orange arrow) are shown. (FIG. 5B) DIC and fluorescence microscope image of a big merged cytocapsula with multiple cells (cell mass) located in the merged and large cytocapsula. Merged cytocapsular tube membranes (MTM, orange arrow) are shown. (FIG. 5C) Quantitation of cell entry. (FIG. 5D) Immunofluorescence microscopy image of endogenous Syncytin-1 in HMECs. (FIG. 5E) Western blot images of Syncytin-1 expression during cytocapsular tube development. (FIG. 5F) Knockdown of Syncytin-1 decreases HMEC cytocapsular tubes mergence. (FIG. 5G) Knockdown of Syncytin-1 does not affect HMEC cytocapsular tubes initiation.

(FIG. 6A) Heat map of the transcriptional changes of 26 integrin genes during cytocapsular tube development. (FIG. 6B) Effects of ITGB-2 on cytocapsula generation and cytocapsular tube elongation.

DETAILED DESCRIPTION

Figure 1A:
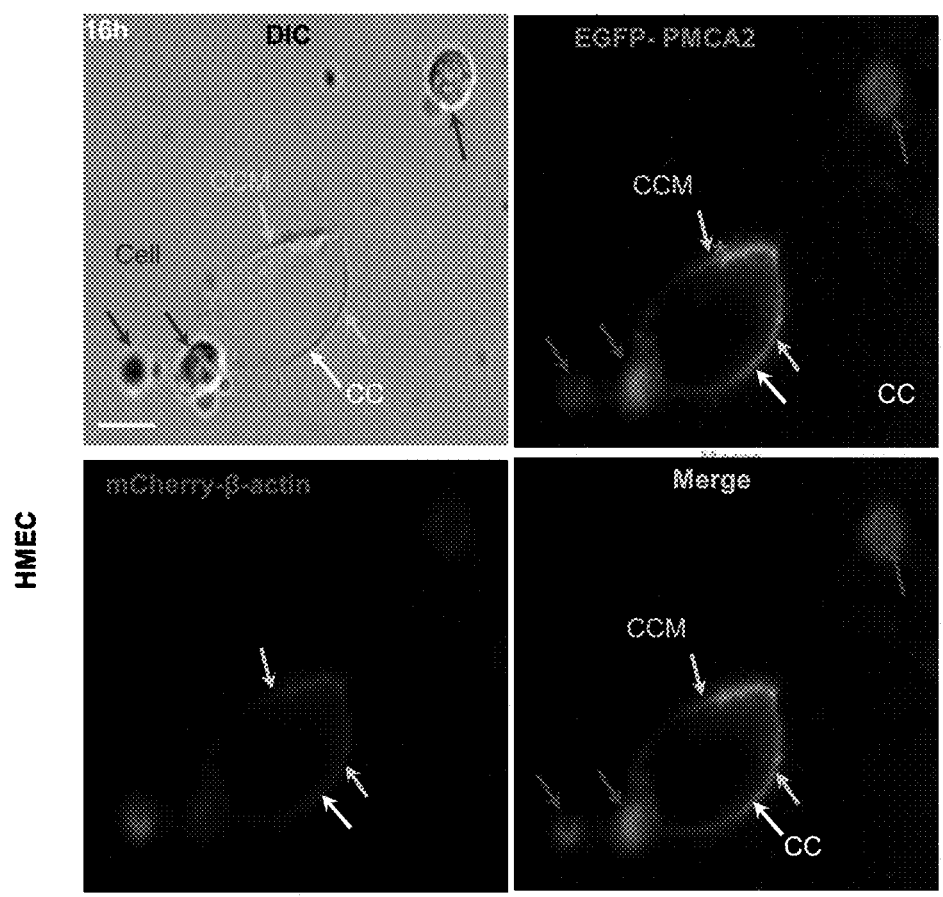
FIGS. 1A-1F depict images for generation of cytocapsulae and cytocapsular tubes.

Aspects of the present disclosure are based on the heretofore undiscovered observation that cells, when implanted and cultured in a controlled 3D extracellular matrix, can generate two novel extracellular membranous organelles, which are herein named cytocapsulae and cytocapsular tubes. Cells migrate in cytocapsulae and engender cytocapsular tubes, which exhibit pleiotropic biological functions and provide tubular routes for directed cell transportation within the matrix. Multiple cytocapsular tubes form and interconnect to produce networks supporting directed cell transportation in diverse directions within the matrix. The present disclosure proposes a mechanism of directed cell translocation via cytocapsular tubes in 3D microenvironments. The presently disclosed methods and compositions for generation of cytocapsula and cytocapsular tubes will facilitate understanding of mechanisms underlying multicellular organism embryo development, organ homeostasis, tissue regeneration, and immune responses, as well as developing therapeutics for the treatment and management of a broad spectrum of diseases and biological processes including but not limited to cell migration, cell sensing, cell stress protection, cell proliferation, cell differentiation, tumor growth, tumor development, tumor metastasis, tumor relapse, and drug resistance.

As observed, the lifecycle of the cytocapsula and cytocapsular tubes generated in a 3D extracellular matrix according to the methods described herein can be outlined as the following. At an initial step, single/individual cells generate small, round, extracellular and membranous cytocapsulae enclosing the cell. Subsequently, cytocapsulae undergo multiple developing phases. First, cytocapsulae proceed to ecellularization. As a consequence of the ecellularization, cytocapsulae is in complete separation of the expulsed cell, and becoming acellular cytocapsulae. Incomplete separation of cytocapsulae and the expulsed cell has also been observed. In case of incomplete separation, the evicted cells remain connected to the acellular cytocapsulae and can reenter the connected acellular cytocapsulae via autoentry and reform closed cytocapsulae with cells in the lumens. Second, cytocapsulae grow and form large (about 100-250 μm in diameter/major axis), round or oval cytocapsulae. The large cytocapsulae can slightly shrink and form shrunk cytocapsulae enclosing the intraluminal cells. On the other hand, other cells from the surrounding environment can enter single large cytocapsulae containing cells, which leads to single cytocapsulae harboring multiple cells. Ecellularization of these large cytocapsulae generate large acellular cytocapsulae, which will shrink, deflate and form large deflated concaved discs (or in irregular morphologies). Third, cells migrate in the cytocapsulae, deforming cytocapsular membranes and engendering elongated cytocapsular tubes. Alloentry of surrounding cells permits multiple cells enter and migrate in cytocapsular tubes. Cell migration (of single cell or multiple cells) in the homogeneous and membrane enclosed cytocapsular tubes is faster than those found in the heterogeneous environments composed of heterogeneous extracelluar matrix (ECM) and other cells and structures. Presumably, within the cytocapsular tubes, the cell migration is free of the hindrance of ECM, cells and structures. Cytocapsular tubes interconnect and form branched, seamless and membranous tubular networks, providing tubular web systems for directed 3D cell transportation/locomotion in diverse directions. The process of ecellularization generates acellular cytocapsulae and cytocapsular tubes. All the acellular cytocapsulae and cytocapsular tubes proceed with rapid self-decomposition.

According to one aspect, a composition comprising a 3D extracellular matrix and cytocapsulae and cytocapsular tubes is provided. In one embodiment, the cytocapsulae and cytocapsular tubes are generated by a single cell implanted in or at the top of the 3D matrix. In one embodiment, the cells are implanted at the top surface of the 3D matrix. Prior to implanting, the cells are processed to a single cell suspension at a density of between about $1\times10$ to about $1\times10^5$ cells/ml.

According to one aspect, the cytocapsulae and cytocapsular tubes enclose the cell that generates the cytocapsulae and cytocapsular tube. According to another aspect, the cytocapsulae and cytocapsular tubes include multiple cells that enter into the cytocapsulae and cytocapsular tubes from surrounding environment. According to still another aspect, the cytocapsulae and cytocapsular tubes undergo ecellularization and espouse the enclosed cell, forming acellular cytocapsulae and cytocapsular tubes that are devoid of cells.

According to certain aspects, a 3D matrix is provided where a plurality of cells in approximately single cell suspension is added in or to the top layer of the 3D matrix. Incubation of the cell implanted 3D matrix under controlled conditions results in the single cell engendering cytocapsulae and cytocapsular tubes.

According to one aspect, the 3D matrix is porous. Porosity can result from polymerization and/or crosslinking of molecules used to make the matrix material. The porosity is controlled by changing the cross-linking density, the chain lengths and the percentage of co-polymerized branching monomers according to methods known to those of skill in the art. According to one aspect, the 3D matrix is porous to the extent that additional reagents can diffuse or otherwise move through the matrix. A porous matrix may be made according to methods known to those of skill in the art. Additional control over the molecular sieve size and density is achieved by adding additional cross-linkers such as functionalized polyethylene glycols.

According to another aspect, the 3D matrix is viscous. The viscosity of the 3D matrix can be adjusted according to any means known in the art.

According to one aspect, the 3D matrix material is chemically inert and thermally stable to allow for various temperatures. According to one aspect, the 3D matrix material is optically transparent. According to one aspect, the 3D matrix material is optically transparent to allow for 3D imaging techniques known to those of skill in the art. According to one aspect, the matrix is sufficiently optically transparent or otherwise has optical properties suitable for deep 3D imaging for high throughput information readout.

According to one aspect, the material used to form the matrix is biodegradable. According to another aspect, the material used to form the matrix is compatible with a wide range of biological and non-biological specimens in situ.

According to one aspect, the matrix material may be a semi-solid medium that can be made from polyacrylamide, cellulose, alginate, polyamide, cross-linked agarose, cross-linked dextran or cross-linked polyethylene glycol. In certain aspects, the semi-solid medium can be attached to a solid support such as a microscope slide, a culture plate, or a flow cell. The solid support can be attached to the bottom surface of the semi-solid medium.

Matrix forming materials include but are not limited to polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art.

Matrix forming materials further include but are not limited to elastin, laminin, proteoglycans (such as heparan sulfate, chondroitin sulfate, and keratin sulfate), and non-proteoglycan polysaccharides (such as hyaluronic acid). In certain embodiments, matrix forming materials can also include proteins including but not limited to fibrillary, Facit, short chain, and basement membrane proteins. In other embodiments, matrix forming materials can further include signal proteins including but not limited to focal adhesion kinase (FAK), talin, vinculin, paxllin, α-actinin, and GTPase. Biodegradable, biocompatible polymers may for example be used as the matrix material, including but are not limited to ethylene vinyl acetate, polyanhydridcs, polyglycolic acid, collagen, polyorthoesters, polylactic acid and polylactic, polyglycolic copolymers (PLG).

According to certain aspects, a matrix is used in conjunction with a solid support. For example the matrix can be polymerized in such a way that one surface of the matrix is attached to a solid support (e.g., a glass surface), while the other surface of the matrix is exposed or sandwiched between two solid supports. According to one aspect, the matrix can be contained within a container.

Solid supports of the present disclosure may be fashioned into a variety of shapes. In certain embodiments, the solid support is substantially planar. Examples of solid supports include plates such as slides, microtitre plates, flow cells, coverslips, microchips, and the like, containers such as microfuge tubes, test tubes and the like, tubing, sheets, pads, films and the like. Additionally, the solid supports may be, for example, biological, nonbiological, organic, inorganic, or a combination thereof.

Certain characteristics of the matrix have been found to be critical for engendering the cytocapsula and cytocapsular tubes in the matrix. For example, the degree of polymerization, protein concentration and viscoelasticity of the matrix affect generation of cytocapsula and cytocapsular tubes. The present disclosure contemplates a wide degree of matrix polymerization from low, about 10%, to full 100% polymerization. The degree of matrix polymerization is also connected to the matrix density and viscoelasticity. In addition, proteins that are present in the matrix or subsequently added to the matrix also affect generation of cytocapsula and cytocapsular tubes. The present disclosure contemplates a final protein concentration within the matrix in the range of between about 2-12 mg/ml. The present disclosure further contemplates a range of pH 4-8 for the matrix. The degree of polymerization, gradient, density and viscoelasiticity of the matrix affect durotaxis of cell migration within the matrix. In one embodiment, the 3D matrix is a Matrigel.

Cells according to the present disclosure include eukaryotic cells, animal cells, plant cells, insect cells including but not limited to fruit fly cells, C. elegant cells, and the like. Exemplary cells include any cell, human or otherwise, including diseased cells or healthy cells. Certain cells include human cells, non-human cells, human stem cells, differentiated cells, induced pluripotent stem cells (iPSCs), genetically modified cells, human pluripotent cells, epithelial cells, endothelial cells, immune cells, muscle cells, mouse stem cells, primary cell lines, immortalized cell lines, primary and immortalized fibroblasts, HeLa cells and neurons, and tumor cells. In one embodiment, the cell is a mammalian cell. In another embodiment, the cell is a human mammary epithelial cell. In certain embodiments, the cell is a stem cell whether adult or embryonic. In one embodiment, the cell is a pluripotent stem cell. In another embodiment, the cell is an induced pluripotent stem cell. In still another embodiment, the cell is a human induced pluripotent stem cell. According to certain aspect, the cell is in vitro, in vivo or ex vivo.

According to another aspect, the present disclosure provides a method of generating cytocapsulae and cytocapsular tubes. In one embodiment, the method includes the steps of implanting cells in or on top of a 3D matrix, and incubating the cell implanted 3D matrix at a temperature suitable for generation of the cytocapsulae and cytocapsular tubes. Incubation temperatures suitable for generation of the cytocapsulae and cytocapsular tubes is around 37° C., with variations for specific cell types. In one embodiment, the 3D matrix is frozen prior to implanting. In certain embodiments, implanting occurs at temperatures in the range of between about 1-45° C., 1-37° C., 1-6° C., and 2-4° C. In other embodiments, the thickness of the 3D matrix is in the range of between about 1-1000 µm, 2-100 µm, 5-50 µm, and 5-10 µm.

According to certain aspects, the cytocapsulae and cytocapsular tubes enclose the cell that generates the cytocapsulae and cytocapsular tubes. According to other aspects, the cytocapsulae and cytocapsular tubes permit exit of the enclosed cell that generates the cytocapsulae and cytocapsular tubes. According to still another aspect, the cytocapsulae and cytocapsular tubes permit entry of multiple cells from surrounding environment.

According to one aspect, the cells are presented as single cell suspension at a density between about $1\times10$ to $1\times10^5$ cells/ml prior to implanting.

The membrane of the cytocapsulae and cytocapsular tubes have certain characteristics. According to one aspect, the membrane of the cytocapsulae and cytocapsular tubes comprises plasma membrane protein $Ca^{2+}$ ATPase 2. According to another aspect, syncytin-1 regulates cytocapsular tube mergence and cell entry. According to still another aspect, growth factors regulates cytocapsula generation and cytocapsular tube development. According to yet another aspect, ITGB-2 mediates cell migration in cytocapsular tubes and regulates cytocapsular tube elongation. According to still another aspect, matrix metalloproteinases mediate cytocapsular tube elongation.

In certain embodiments, the 3D matrix comprises bioactive and/or bioinactive agents including but not limited to collagen, Matrigel matrix material, elastin, laminin, proteoglycans (such as heparun sulfate, chondroitin sulfate, and keratin sulfate), non-proteoglycan polysaccharides (such as hyaluronic acid), proteins (such as fibrillary, Facit, short chain, and basement membrane proteins) and signal proteins (such as FAK, talin, vinculin, paxllin, α-actinin, and GTPase).

According to another aspect, a method of producing cytocapsulae and cytocapsular tubes in vitro is provided. In one embodiment, the method includes the steps of: implanting cells in a single cell suspension onto the top layer of a 3D matrix; and culturing the implanted cells in a suitable medium and at a suitable temperature wherein each single cell engenders cytocapsulae and cytocapsular tubes in the 3D matrix.

According to still another aspect, a method of preparing a 3D matrix suitable for the generation of cytocapsulae and cytocapsular tubes is provided. In one embodiment, the method comprises: freezing the 3D matrix, and thawing the 3D matrix a suitable temperature. Temperatures suitable for thawing the matrix are between about 1-45° C., 1-37° C., 1-6° C., and 2-4° C.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example I

Generation of Cytocapsulae and Cytocapsular Tubes.

Figure 1B:
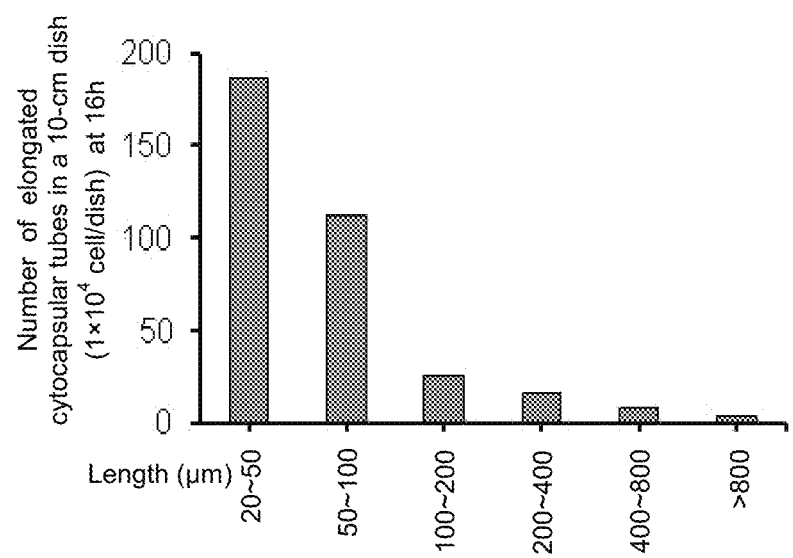
Figure 1C:
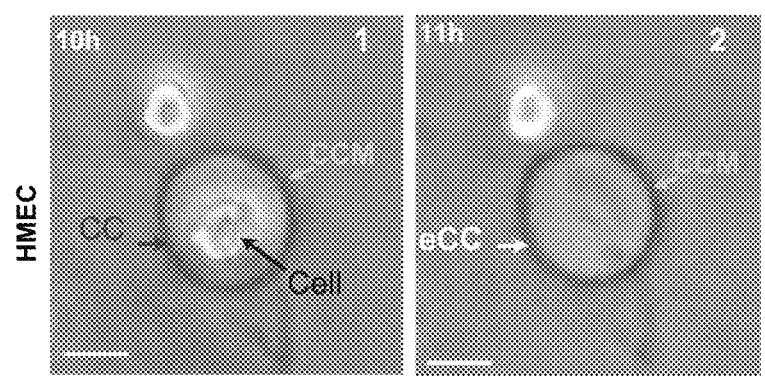
Figure 1D:
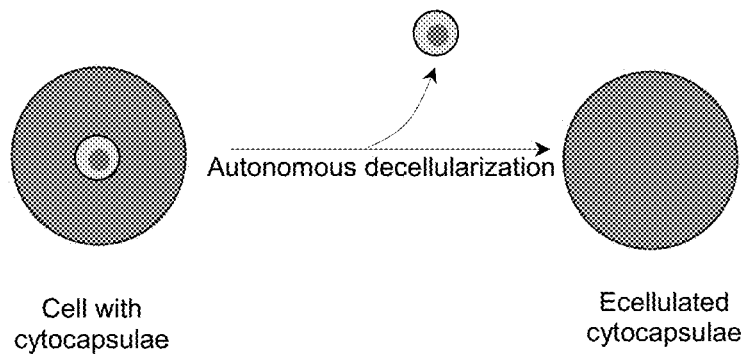
Figure 1E:
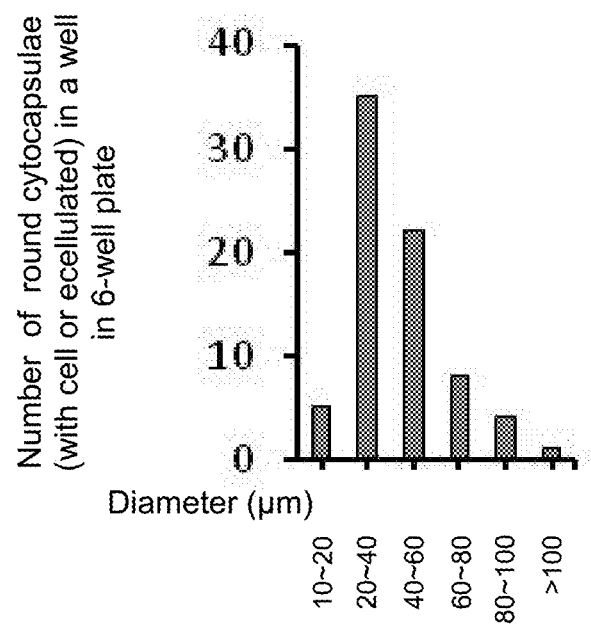
Figure 1F:
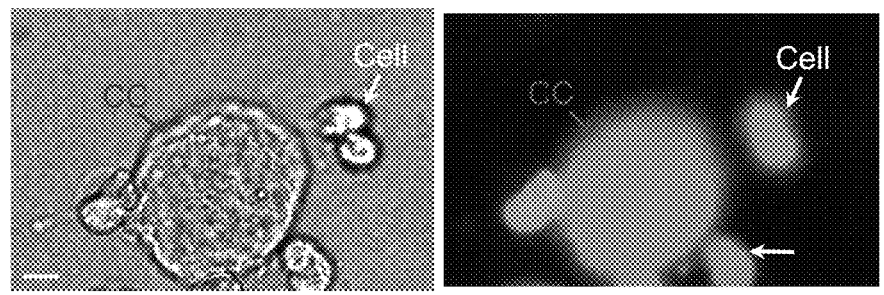

To investigate mechanics of cellular boundary and 3D cell locomotion, normal primary human mammary epithelial cells (HMECs) were implanted in a 3D Matrigel matrix, a reconstituted extracellular matrix (ECM) surrogate according to certain embodiments of the present disclosure. The single spherical HMECs in 3D Matrigel, but not the cells in 2D environments, have generated round/irregular shaped and extracellular bubble-like capsulae in variable sizes enclosing the cell (FIG. 1A). Approximately 96% of single HMECs (1x $10^3$ cells/well in 6-well plates, n=3) engendered extracellular capsulae at 12 h. The diameter/major axis of extracellular spherical/oval capsulae significantly increased, and reached up to 250 µm. To confirm whether the capsular surface is membranous, we transiently overexpressed in HMECs enhanced green fluorescence protein (EGFP) fusion with plasma membrane protein $Ca^{2+}$ ATPase 2 (EGFP-PMCA2). Indeed, EGFP-PMCA2 is distributed throughout both the plasma membrane of cells and extracellular capsulae membranes, which verified that the extracellular capsulae are enclosed by membranes (FIG. 1A). These extracellular cytocapsulae can elongate to form long tubes in variable lengths (FIG. 1B). Over time, the single capsulae automatically ecellularized, leaving acellular and closed capsulae in multiple morphologies (spherical, oval, or irregular) with taut membranes (FIGS. 1C-1D). These cytocapsulae are in various sizes and can be large up to 100 µm in diameter (FIG. 1E). These cytocapsulae are membranous (FIG. 1F). These observations evidenced that the capsular membrane independently locate outside of the plasma membrane, and that acellular capsulae can exist without the cell. This previously unappreciated, single mammalian cell generated, extracellular, membranous capsula was termed as cytocapsula.

Example II

Cytocapsula Ecellularization.

In most instances, after cytocapsular ecellularization, the cell is completely separated from its acellular cytocapsula. The acellular cytocapsulae collapse and form deflated and concaved discs (FIG. 1C). Sometimes, cytocapsula ecellularization results in incomplete separation of the expulsed cell from its acellular cytocapsula.

After ecellularization, the growth of acellular cytocapsulae terminated, strongly suggesting that cytocapsula's generation and growth depends on the intraluminal cell. Meanwhile, the big gap/distance between the plasma membrane and extracellular capsular membrane indicated that the capsular components originated from the intraluminal cell are released/delivered outside of the plasma membrane for cytocapsular building (FIG. 1C). Subsequently, the acellular cytocapsulae continued to shrink and deflate, and cytocapsular membranes folded, forming large, deflated and concaved discs, or short flat tubes. After about 0.5-1 h, acellular cytocapsulae's membranes degraded and cytocapsulae self-decomposed. These observations suggested that the lifecycle of cytocapsula proceeds through several successive and distinct phases: from initiation, growth, ecellularization, deflation and shrinkage, membrane degradation, to auto-decomposition.

Cell contact at high cell density diminishes cytocapsula generation and significantly increases cytocapsula decomposition. Cell contact inhibition at high cell density does not completely suppress cytocapsula generation or entirely induce cytocapsula decomposition. Cell contact at high cell density declines cytocapsula growth in diameter.

Figure 2:
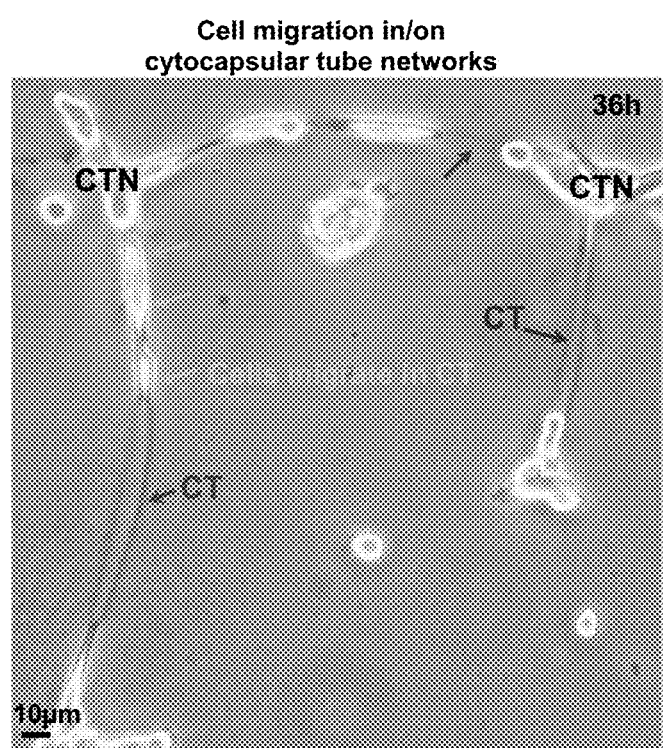
FIG. 2 depict the HMEC cytocapsular tube networks. HMEC migration in cytocapsular tubes and network formation. Cytocapsular tubes (CT, red arrows), cytocapsular tube connection node (CTN), multiple cells migrating in a single cytocapsular tube (orange arrows), and cell mass with no cytocapsular tubes (black arrow) are shown.

Over time, single cells migrate bi-directionally in its cytocapsulae, deform cytocapsular membranes, and generate elongated cytocapsulae, forming membranous tubes in variable lengths (FIG. 2). Afterwards, the intraluminal cells were expulsed from cytocapsular tubes. Ecellularization of cytocapsular tubes produced acellular cytocapsular tubes. Then, the long acellular cytocapsular tubes automatically shrank, and membranes severely folded, forming deflated, coiled, twisted, and membrane condensed strands. Subsequently, the membranes of the long shrunk and acellular cytocapsular tubes degraded, followed by tube auto-decomposition. These sequentially developmental stages of cytocapsular tubes of single cells demonstrated that the lifecycle of cytocapsular tubes progressively proceed from single cell migration in its cytocapsulae to cytocapsular membrane deformation, cytocapsula elongation, cytocapsular tube formation, ecellularization, and acellular cytocapsular tube auto-decomposition.

Single HMECs generated cytocapsular tubes can reach up to 820 µm in length. Increased cell density decreases average cytocapsular tube lengths, but not the average widths (approximately 11 µm in diameter/width). Moreover, high cell density leads to reduced average lifetime of cytocapsular tubes. In addition, high cell density diminishes average cytocapsular tube density (in length and number). Some cytocapsular tubes can endure compacted microenvironments.

Next, we assessed breast cancer stem cells of HMLER ($CD44^{high}/CD24^{low})^{FA}$ subpopulations (Yi T, et al. (2014) Quantitative phosphoproteomic analysis reveals system-wide signaling pathways downstream of SDF-1/CXCR4 in breast cancer stem cells. *Proceedings of the National Academy of Sciences of the United States of America* 111(21): E2182-2190) on cytocapsular generation. At the low cell densities of $1 \times 10^2$ and $1 \times 10^3$ cells/well, approximately 99% BCSCs generated cytocapsulae at 15 h in 3D Matrigel. BCSC cytocapsulae have more ability in withstanding cell contact inhibition. BCSC cytocapsular tubes are statistically longer than those of HMECs, and single BCSC cytocapsular tubes can reach up to 1000 µm in length.

Example III

Cytocapsula and Cytocapsular Tube are Extra-Plasma Membrane Organelles.

The inventors have discovered that cytocapsula and cytocapsular tube are neither extensions of the plasma membrane nor cell surface connected. They are generated by single cells, surrounded by their own engendered membrane distinct from the plasma membrane and enclosing the cell that generated them. Besides the pleiotropic biological functions, the cytocapsula and cytocapsular tube have unique characters including: extracellular membranous capsulae (or tubes) enveloping the cell, and permission of ecellularization and cell entry. On the other hand, the cytocapsular tube, but not the cytocapsula, supplies with long tubular avenues for directed transportation of multiple cells. Cytocapsulae and cytocapsular tubes are not the extensions of plasma membrane, and are extracellular membranous organelles enveloping the cells. Cytocapsulae and cytocapsular tubes do not present in the 2D cell cultures. Cytocapsulae and cytocapsular tubes have pleiotropic biological functions, including providing supporting scaffolds and coverings for enclosed cells, permitting ecellularization and cell entry. Cells can migrate in cytocapsulae, cytocapsular tubes, and cytocapsular tube networks. Auto-decomposition of cytocapsulae and cytocapsular tubes does not affect cell survival, proliferation and growth. Ecellularized cytocapsulae and cytocapsular tubes can exist up to 98 hours. Cytocapsulae and cytocapsular tubes can accommodate multiple such as dozens of cells. Cytocapsular tubes interconnect and form open tubular networks for directed cell translocation in multiple directions. These characteristics of the cytocapsula and cytocapsular tubes demonstrate that they are two novel facultative organelles that are distinct from all previously described organelles.

Example IV

The Formation of Cytocapsular Tube Networks.

At 6 h, single primary normal HMECs generated large, membranous and short cytocapsular tubes in the indicated Matrigel matrix (FIG. 2). At 10 h, HMEC migrated in the short cytocapsular tubes and generated elongated cytocapsular tubes (FIG. 2). At 36 h, multiple HMEC long cytocapsular tubes interconnected and formed networks via connection nodes. (FIG. 2). At 68 h, HMECs aggregated and formed cell masses, all the HMEC cytocapsular tubes decomposed and no cytocapsular tube remained (FIG. 2).

Figure 3A:
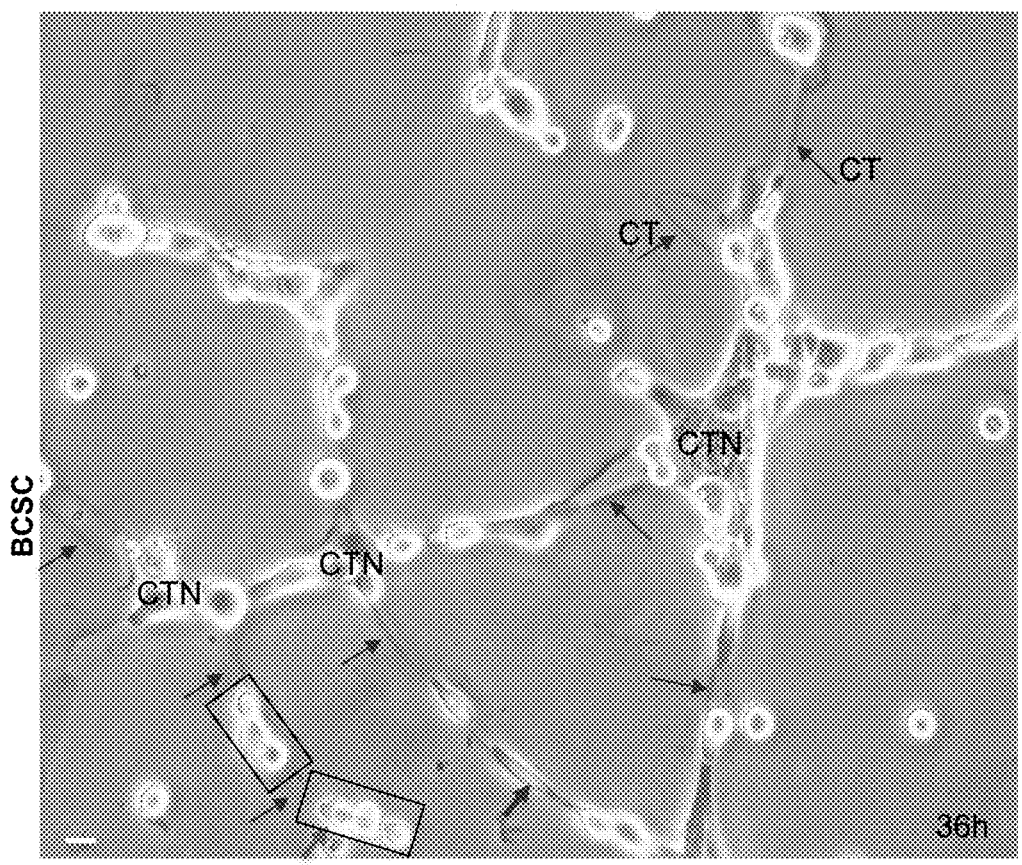
FIGS. 3A-3B depict architectures of cytocapsular tube networks.
Figure 3B:
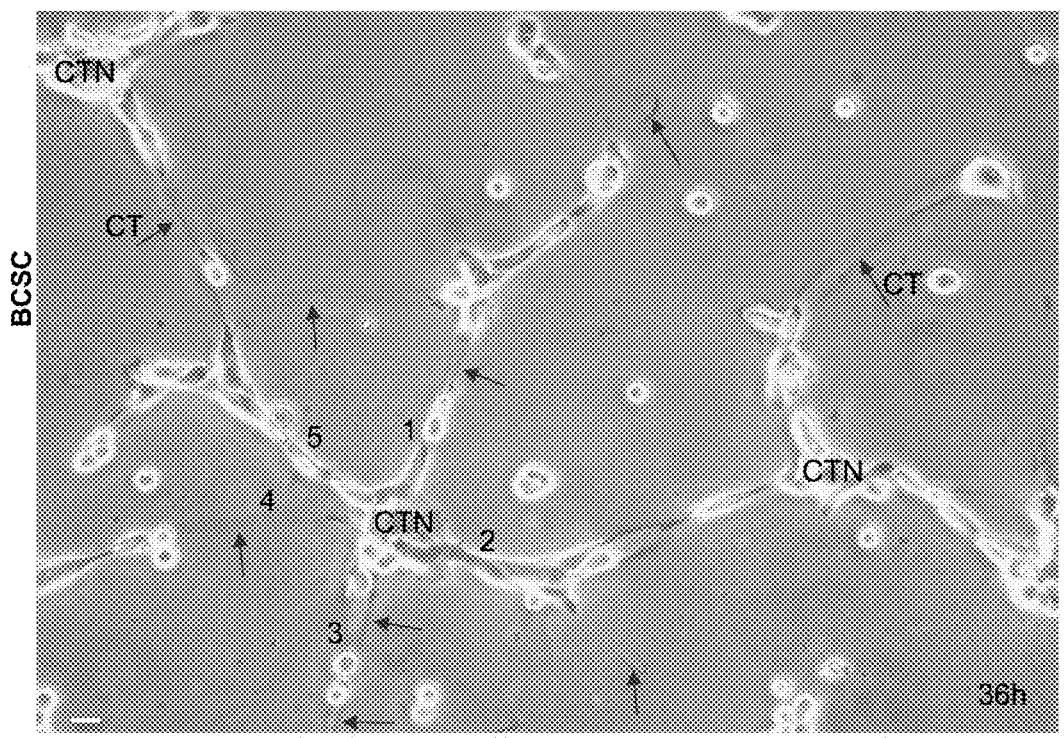
Figure 4:
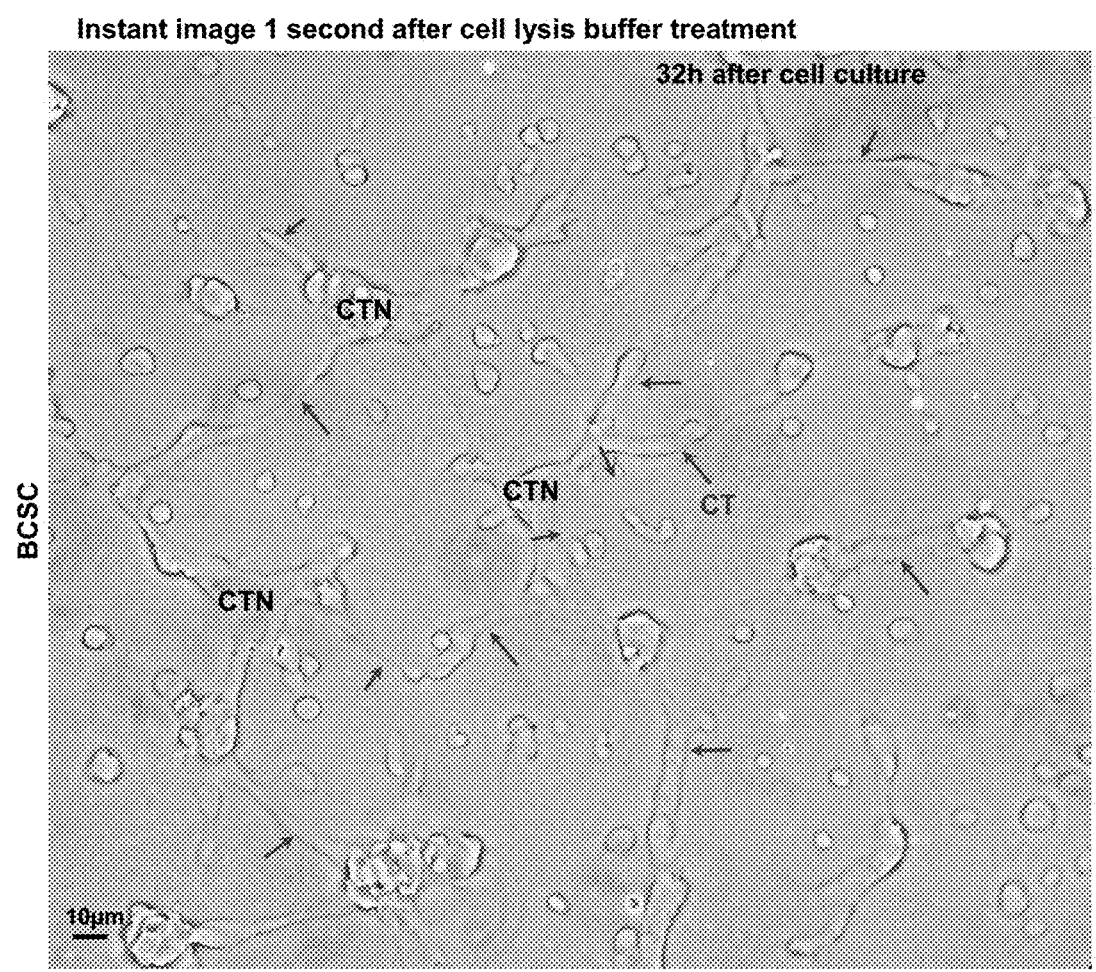
FIG. 4 depict instant imaging with cell lysis analyses of BCSC cytocapsular tubes network systems. Bright field image of cytocapsular tube networks by instant imaging with cell lysis. The nested cytocapsular tubes (CT, red arrows) and cytocapsular tube node (CTN) in a cytocapsular tube network are shown. Images were taken at 1-2 seconds after cell lysis buffer treatment. At the 3rd second after lysis buffer treatment, all the cytocapsular tubes and cell plasma membranes were lysed, and disappeared.

At 4 h, breast cancer stem cells (BCSCs) already generated large and short cytocapsular tubes in the indicated 3D Matrigel matrix (FIG. 3A). BCSCs migrated bi-directionally in the cytocapsular tubes, deformed cytocapsular membranes and shaped the tube morphologies, and engendered long and curved cytocapsular tubes (FIG. 3B). Multiple BCSC cytocapsular tubes connected and formed various morphologies, including closed circles. Many cancer cells migrated in the cytocapsular tubes in diverse formats, including streaming and linear (FIG. 3). Later, BCSCs aggregated and formed spherical or irregular shaped tumor spheres. Next, we quantitated BCSC cytocapsular tube lengths along time. BCSC cytocapsular tubes can reach up to 1000 μm in length. Multiple cytocapsular tubes can connect to form longer tubes. The number of cytocapsular tubes decreased along time, indicating that the lengths of cytocapsular tubes are dynamically and tightly controlled (FIG. 4).

The aforementioned data demonstrated that cytocapsular tubes generally proceed successive but distinct phases: cytocapsula initiation, cell migration in cytocapsulae, cytocapsula elongation and form cytocapsular tubes, multiple cytocapsular tunes connect and form networks, cells migrate in cytocapsular tube networks, cell aggregation and cell mass/cluster formation, and cytocapsular tube decomposition.

Two or more HMEC cytocapsular tubes of variable lengths interconnect and form tubular networks via connection nodes. At 38 h, BCSCs developed many more cytocapsular tube connection nodes than HMECs. In addition, the average number of cytocapsular tubes per connection node of BCSCs is larger than that of HMECs. The cytocapsular tube density of BCSCs is about 3-fold higher than that of HMECs. These data demonstrated that the BCSCs have more aggressive capacity to generate interconnected cytocapsular tube networks. The lifetime of BCSC cytocapsular tubes with cells, isolated or connected, is much longer than that of acellular BCSC cytocapsular tubes, indicating that the intraluminal cells facilitate maintaining tubes against decomposition. Compared to isolated BCSC cytocapsular tubes with cells, connected BCSC cytocapsular tubes with cells statistically stay intact for longer duration. These results suggested that cytocapsular tube maintenance is tightly controlled and mediated by the intraluminal cells. Importantly, BCSC cytocapsular tubes interconnect and form tubular networks in tumors in vivo, and multiple cells migrate in these tubular networks. These data demonstrated that cytocapsular tube networks provide membranous tubular webs for directed cell locomotion in diverse directions.

Example V

Cytocapsular Tubes Highway for Cell Transportation.

Cells migrate in membranous cytocapsular tube networks, in which tubular cytocapsular tubes provide highways for cell translocation (FIGS. 2-3). Using fast cell lysis and instant image technologies, we examined the cytocapsular tube network architectures. BCSC cytocapsular tubes broadly and aggressively interconnect, significantly form crosses, open circles, closed circle, and many other irregular morphologies, providing super-large tubular networks for cancer cell directed cell relocation to far destinations in multiple directions (FIG. 4). Both single and multiple cells migrate faster in cytocapsular tubes compared to that in the 3D environments. Cytocapsular tubes form highways for directed 3D cell transportation.

Example VI

Syncytin-1 Regulates Cytocapsular Tube Mergence and Cell Entry.

Figure 5A:
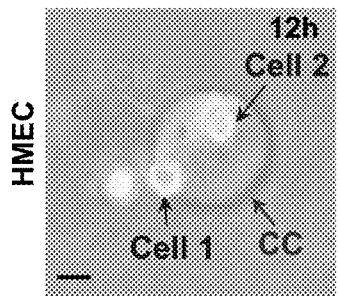
FIGS. 5A-5G depict cytocapsula mergence and cell entry.
Figure 5B:
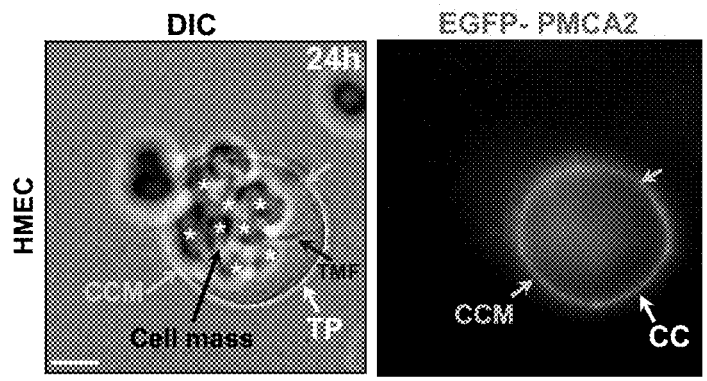
Figure 5C:
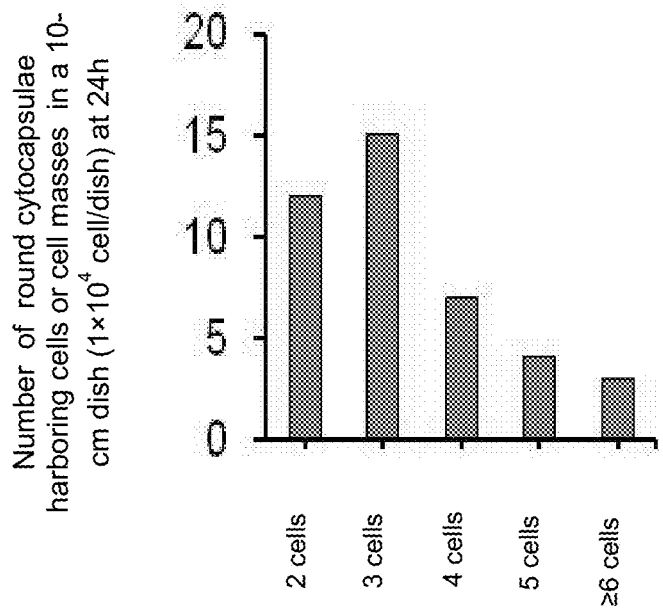
Figure 5D:
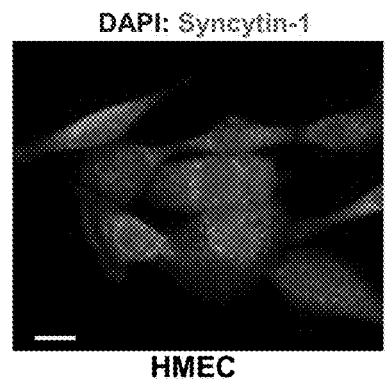
Figure 5E:
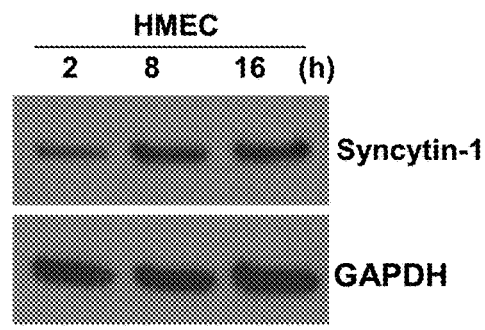
Figure 5F:
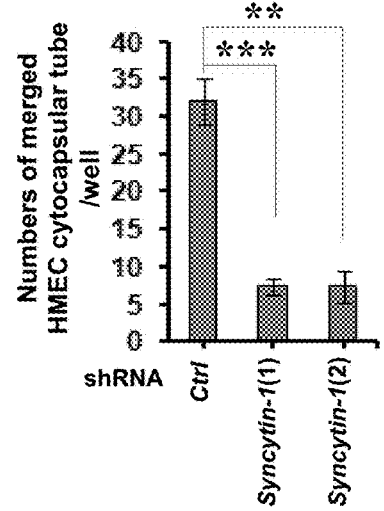
Figure 5G:
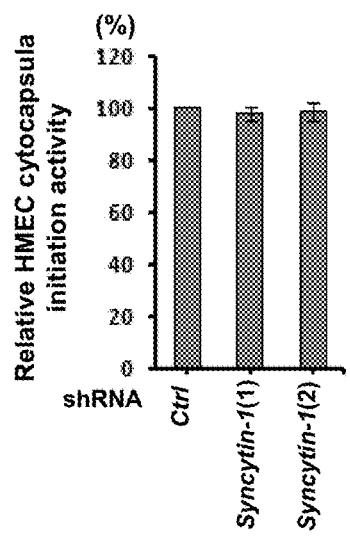

Cytocapsulae of different cells can merge and form larger cytocapsulae and cells can enter other cells' cytocapsulae (FIG. 5A). Cells can enter other cells' cytocapsulae, leading to single large cytocapsulae harboring multiple cells or cell masses (FIGS. 5B-5C). Next, we probed the molecular mechanisms underlying cytocapsular tube fusion, mergence and cell entry. Endogenous membrane fusion protein Syncytin-1 was expressed in HMECs, cytocapsulae and cytocapsular tube. Transient knock down of Syncytin-1 in HMECs significantly decreased cytocapsular tube elongation, connection, but not the cytocapsula initiation (FIGS. 5D-5F). In addition, Syncytin-1 protein levels increased during cytocapsular tube elongation (FIG. 5G). These data demonstrated that Syncytin-1 regulates cytocapsular tube mergence and cell entry.

Example VII

Integrin Subunit Beta-2 (ITGB-2) Promotes Cytocapsular Tube Development.

Figure 6A:
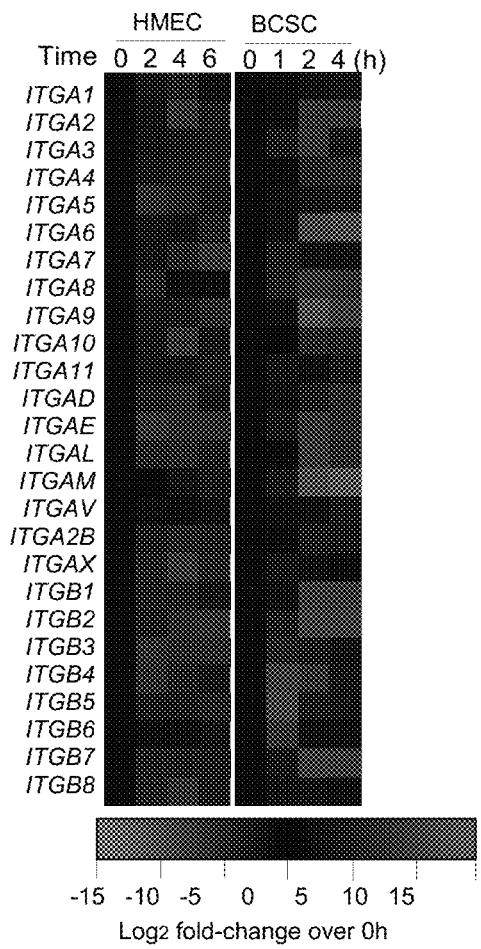
FIGS. 6A-6B depict ITGB-2 regulating cytocapsular tube elongation.
Figure 6B:
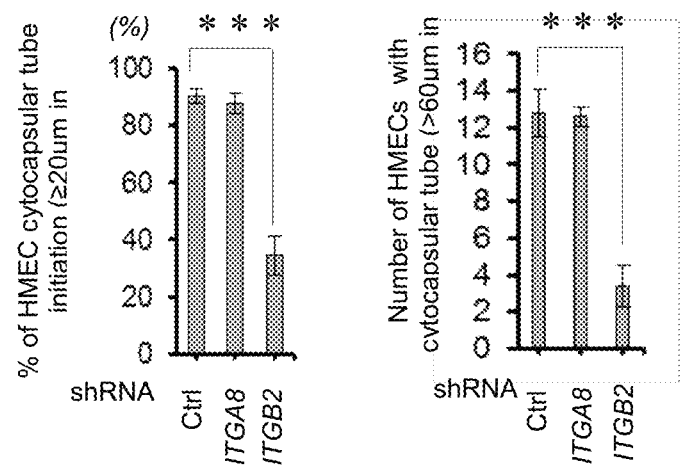

Integrins are cellular surface supporting molecules essential for cell adhesion, attachment, migration and invasion. We examined 26 integrin gene transcripts in BM-MSC, HMECs and BCSCs during cytocapsular tube development. ITGB-2 significantly increases along the course of cytocapsular tube elongation (FIG. 6A). Furthermore, transient knock down of ITGB-2, but not ITGA-8, with gene specific shRNAs leads to significantly decreased cytocapsular tube elongation (FIG. 6B). These data demonstrated that ITGB-2 mediates cell migration in cytocapsular tubes and regulates cytocapsular tube elongation.

In sum, the present disclosure provides that single cells generate two novel organelles, the extracellular and membranous cytocapsulae and cytocapsular tubes, and that cytocapsular tubes provide tubular freeways for 3D cell transportation. Cell locomotion in multicellular organisms is critical for embryonic development, tissue formation, organ homeostasis, immune responses, wound healing, tissue regeneration, and tumor metastasis.

The generation and development of cytocapsulae and cytocapsular tubes highly depend on both 3D environment and cellular activities, and, in the study, they are brought into focus only when the 3D matrix's biochemical, biophysical and biomechanical characters (such as polymerization, density and viscoelasiticity) are in a precisely controlled manner. The temporospatial appearance, self-degradation and auto-decomposition of cytocapsulae and cytocapsular tubes all contribute to the difficulty in realizing and identifying these previously unidentified organelles.

Cytocapsular membranes provide substantial bio-membranous scaffolds supporting cellular adhesion, attachment, detachment, morphological transition and motility plasticity. On the other hand, cytocapsulae envelop the cells, physically shielding them from the extra-cytocapsular microenvironments, which facilitate the stringent spherical cells to interconvert into relaxed irregular morphologies, and might serve as protective coverings against the environmental stresses. Cytocapsular tubes supply membranous tubes that accommodate directed migration and bi-directional locomotion of multiple cells. More importantly, cytocapsular tubes interconnect and form tubular networks, which significantly increase cell migration directions, amplify cell spreading areas, and augments directed 3D cell migration efficiency. Although cell contact inhibition at high cell density diminishes cytocapsula generation, increases cytocapsula decomposition, and reduces cytocapsular tube duration, there are still approximately 1.2‰ normal cells (HMECs) and up to 1.1% breast cancer stem cells that generate cytocapsulae, and engender long capsular tubes for directed migration of multiple cells. Therefore, compared to the format that all cells are unavoidably exposed to and experience heterogeneous obstacles sourced from compacted and heterogeneous 3D ECM and cells in vivo, the form that a small percentage of cells generate homogeneous membranous cytocapsular tubes serving highways for directed transportation of multiple cells is an efficient one, at least an alternative pattern. Cytocapsulae and cytocapsular tubes exhibit potentials of pleiotropic biological functions, and other functions need more work to elucidate.

The enlargement of cytocapsulae depends on the activities of the intraluminal cell and acellular cytocapsulae terminate growth. On the other hand, acellular cytocapsulae and cytocapsular tubes proceed rapid auto-degradation and self-decomposition. In addition to intracellular organelles, eukaryotic cells contain extracellular organelles that are released or shed into the microenvironments, such as exosomes (Keller S, Sanderson M P, Stoeck A, & Altevogt P (2006) Exosomes: from biogenesis and secretion to biological function. *Immunology letters* 107(2):102-108). Interestingly, there are a number of various, single-layered membrane enclosed vesicles in the cytocapsular tube lumens. Therefore, these membranous vesicles may functionally link to the carriers or cargoes that deliver/shuttle cell-originated cytocapsular components, and to containers that include lysates whose release results in the tightly controlled auto-decomposition of cytocapsulae and cytocapsular tubes.

The phenomena that, after ecellularization, acellular cytocapsular tubes shrink, contract, and become deflated, shortened, twisted and folded strands, are in agreement with the lack of intraluminal skeleton in cytocapsular tubes. The absence of microfilament networks in the cytocapsular tube lumens is consistent with that single and multiple cells actively migrate in cytocapsular tubes. On the other hand, the present of microfilament scaffolds under cytocapsular tube membranes agrees with the fact that the long cytocapsular tubes can be dragged by the cell to cross ECM surfaces without breakage, interruption or interception.

Cell migration in its cytocapsulae drives cytocapsular membrane deformation and elongation, and cytocapsular tube formation and elongation. The building of membranes and other components in cytocapsulae and cytocapsular tubes requests plenty of variable proteins, which suggested that mRNA translation and/or protein biosynthesis is essential for the development of cytocapsulae and cytocapsular tube.

In summary, the two novel organelles of cytocapsula and cytocapsular tube uncovered in this study present pleiotropic biological functions, including supplying with tubular pathways and networks for cell transportation, relocation and migration, which may provide insights into understanding the mechanisms of cell protection, and translocation involved processes in development and pathogenesis of diseases, including tumor metastasis.

Example VIII

Materials and Methods

Cells and Reagents.

Primary normal human mammary epithelial cells (HMECs) were ordered from ATCC (PCS-600-010™). BCSCs of HMLER ($CD44^{high}/CD24^{low})^{FA}$ subpopulation cells were prepared as previously described(27). FITC-conjugated anti-CD44 (BD Biosciences; G44-26) antibody and phycoerythrin-conjugated anti-CD24 (BD Biosciences, ML15) antibody were used for cell sorting with flow cytometry. MEGM™ Mammary Epithelial Cell Growth Medium BulletKit™ (Clonetics™ MEGM™ Mammary Epithelial Cell Growth Medium plus SingleQuots™ Kit package) were ordered from Lonza (CC-3150). Matrigel™ Membrane Matrix (CB-40234) was purchased from Corning. BD Matrigel Matrix Growth Factor Reduced (GFR, catalog number 356230) was ordered from BD Bioscience.

Time-Lapse DIC Microscopy, Transient Transfection, Quantitative Real-Time PCR, and Transient Gene Knockdown.

Time-lapse DIC (differentiation interference contrast) microscopy analyses of cytocapsula elongation and cell migration were performed using a Nikon Ti motorized inverted microscope and a digital Hamamatsu ORCA-ER cooled CCD camera with a 20× lens. HMEC cultures with cytocapsulae in Matrigel Matrix (>40 μm in depth) were analyzed with TEM. Plasmids of EGFP-hPMCA2z/b (Addgene, #47584) and/or mCherry-β-actin (#54967) were co-transfected into HMECs using Lipofectatine® 2000. Quantitative real-time PCR assays were performed using gene specific primers (IDT Company), iQ SYBR® Green Supermix (Bio-Rad), and 7900HT Fast Real-Time PCR.

Reagents and Antibodies.

EGFP-hPMCA2z/b (#47584) and mCherry-β-actin (#54967) plasmids were ordered from Addgene. Anti-GAPDH (catalog number 2118S, 1:1000 dilution in Western blot assay) antibodies were ordered from Cell Signaling Technology. DAPI (4, 6-diamidine-2-phenylindole, dihydrochloride, 1:1000 dilution in immunofluorescence assay) was ordered from KPL. Anti-γ-Actin (gamma Actin, monoclonal, ab123034, 1:1000 dilution in immunofluorescence assay), Anti-pan-Cadherin (polyclonal, ab140338, 1:1000 dilution in immunofluorescence assay) antibodies were ordered from Abcam.

Transient Transfection.

HMECs were cultured with MEGM at 37° C. in a humidified atmosphere of 5% $CO_2$. Plasmids of EGFP-hPMCA2z/(Addgene, #47584) and/or mCherry-β-actin (#54967) were co-transfected into HMECs using Lipofectatine® 2000 (Life Technologies, #11668027), according to the manual. Two days after transfection, the cells were used for assays.

Development of Cytocapsulae and Cytocapsular Tubes.

The HMECs (with/without transfection), BM-MSC, and BCSCs of HMLER($CD44^{high}/CD24^{low})^{FA}$ subpopulations were plated on a Matrigel matrix layer at the indicated cell densities (or $5\times10^2$ cells/well in 6-well-plate, or $1.2\times10^4$ cells in 10 cm dishes, if not indicated) in MEGM media. The 3D Matrigel layers (>40 μm in depth) were prepared by quickly adding cold and thawed Matrigel matrix (thawed in ice at 4° C. cold room for overnight, with protein concentrations of 4-12 mg/ml) to pre-chilled 6-well-plates (with/without cold micro cover glasses), followed by addition of cold MEGM (4° C.) and incubation in the hood at room temperature (25° C.) for 5-25 minutes. Then, the cells were implanted on the 3D Matrigel gel surface and cultured in a humidified incubator (37° C., 5% $CO_2$). Cells in (or invaded into) the Matrigel gel in variable layers and generate cytocapsulae and cytocapsular tubes. The developed cytocapsulae and cytocapsular tubes in various stages were used in this study.

Time-Lapse DIC Microscopy and Videos.

Time-lapse DIC (differentiation interference contrast) microscopy analyses of cytocapsula elongation and cell migration were performed using a Nikon Ti motorized inverted microscope and a digital Hamamatsu ORCA-ER cooled CCD camera with a 20× lens. The time-lapse microscope was equipped with DIC, phase contrast, and epifluorescence optics, a Prior Proscan III motorized stage and shutters, a perfect focus system, and an OkoLab 37° C., 5% $CO_2$ cage microscope incubator (OKO Lab). Images were taken every 30 s over the course of 10~36 h. All images were obtained using MetaMorph software. Tracks made by 2 h of cytocapsula elongation were obtained using MetaMorph and ImageJ software. Cytocapsula elongation velocities were also calculated using length and time measurements. Videos were prepared using the images collected via time-lapse and MetaMorph software (15 frames per second, fps).

Imaging Acquisition.

Differential interference contrast (DIC) and fluorescence images of fixed cells (with/without cytocapsulae) were taken with an 80i upright microscope and a digital Hamamatsu ORCA-ER cooled CCD camera with a 20× or 40× lens. The bright field phase contrast image was taken using a Nikon digital camera. The cytocapsula initiation ratio/high performance field (HPF, 200×) and the number of elongated cytocapsulae/HPF were quantified. All images were obtained using MetaMorph image acquisition software, and analyzed with ImageJ software.

Total RNA Extraction and Quantitative Real-Time PCR.

TRIzol® (Thermo Fisher Scientific) was used to extract total RNAs from HMECs and the BCSCs ($1.2\times10^4$ cells per 10 cm dish) with and without detectable cytocapsulae, at the indicated times. The samples used were those plated on the Matrigel matrix layers (about 10 μm thick). Total RNAs were extracted as the manual described. Quantitative real-time PCR assays were performed using gene specific primers (IDT Company), iQ SYBR® Green Supermix (Bio-Rad), and 7900HT Fast Real-Time PCR according to the manufacturer's instructions. GAPDH was used as a control, and three independent experiments were performed. Data analyses and heatmap figures were calculated and prepared as previously described.

Western Blotting.

Using a radioimmunoprecipitation assay (RIPA) buffer (25 mM Tris-HCl pH 7.6, 150 mM NaCl, 1% NP-40, 1% sodium deoxycholate, 0.1% SDS) and protease inhibitor (Roche), total proteins were extracted from the HMECs, and BCSCs ($1.2\times10^4$ cells per 10 cm dish) at the indicated times, both with and without cytocapsulae. The samples used were those implanted onto Matrigel matrix layers. The total proteins were eletrophoresed through 10% or 12% SDS-polyacrylmide gels and transferred onto polyvinylidene difluoride Immobilon™-P membranes. Polyvinylidene difluoride membranes were probed with primary antibodies (Anti-GAPDH (Cell signaling Technology, 2118, 1:1000), for 4 h at 4° C. followed by washing in 0.1% Tween/TBS. Membranes were incubated with appropriate peroxidase-conjugated secondary antibodies at 25° C. or 1 h and washed thrice prior to signal detection. ECL™ Western blotting detection reagent was used for development.

Quantification and Statistical Analysis

In all figures: no significance, ns, $P>0.05$; *$P<0.05$; $P<0.01$; *$P<0.001$.

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference herein in their entirety for all purposes to the same extent as if each individual publication or patent application was specifically indicated to be so incorporated by reference.

We claim:

1. A composition comprising a 3D matrix and cytocapsulae and cytocapsular tubes, wherein the cytocapsulae and cytocapsular tubes are generated by implanting a single cell suspension on top of the 3D matrix at between about 1-6° C., and culturing the cells of the single cell suspension at 37° C., wherein the cells of the single cell suspension comprise human mammary epithelial cells (HMECs) or breast cancer stem cells (BCSCs), and wherein the 3D matrix is a gelatinous protein mixture sold under the trade name Matrigel.

2. The composition of claim 1 wherein the 3D matrix is biodegradable.

3. The composition of claim 1 wherein the 3D matrix comprises elastin, laminin, collagen, proteoglycans, and/or non-proteoglycan polysaccharide.

4. The composition of claim 1 wherein polymerization, density, protein concentration, and viscoelasiticity of the 3D matrix affect the generation of the cytocapsulae and cytocapsular tubes.

5. A method of generating cytocapsulae and cytocapsular tubes in vitro comprising the steps of:
   implanting a single cell suspension of cells on top of a 3D matrix at between about 1-6° C., wherein the cells of the single cell suspension comprise HMECs or BCSCs, and wherein the 3D matrix is a gelatinous protein mixture sold under the trade name Matrigel; and
   incubating the cells of the single cell suspension on top of the implanted 3D matrix at 37° C.,
   thereby generating cytocapsulae and cytocapsular tubes.

6. The method of claim 5 wherein the 3D matrix is kept frozen prior to implanting.

7. The method of claim 5 wherein implanting occurs at between about 2-4° C.

8. The method of claim 5 wherein the 3D matrix is biodegradable.

9. The method of claim 5 wherein the 3D matrix comprises elastin, laminin, collagen, proteoglycan, and/or non-proteoglycan polysaccharide.

10. The method of claim 5 wherein polymerization, density, protein concentration, and viscoelasiticity of the 3D matrix affect the generation of the cytocapsulae and cytocapsular tubes.

11. The method of claim 5 wherein the thickness of the 3D matrix is between about 3 to about 100 μm in thickness.

12. The method of claim 5 wherein the cytocapsulae and cytocapsular tubes enclose the cell that generates the cytocapsulae and cytocapsular tubes.

13. The method of claim 5 wherein the cytocapsulae and cytocapsular tubes permit exit of the enclosed cell that generates the cytocapsulae and cytocapsular tubes.

14. The method of claim 5 wherein the cytocapsulae and cytocapsular tubes permit entry of multiple cells from surrounding environment.

15. The method of claim 5 wherein the cells are presented as single cell suspension at a density of between about $1\times10$ to about $1\times10^5$ cells/ml prior to implanting.

16. The method of claim 5 wherein the membrane of the cytocapsulae and cytocapsular tubes comprise plasma membrane protein Ca2+ ATPase 2.

17. The method of claim 5 wherein syncytin-1 regulates cytocapsular tube mergence and cell entry.

18. The method of claim 5 wherein ITGB-2 mediates cell migration in cytocapsular tubes and regulates cytocapsular tube elongation.

19. The method of claim 5 wherein the 3D matrix further comprises bioactive and/or bioinactive agents.

20. The method of claim 5, further comprising freezing the 3D matrix prior to implanting.

* * * * *